United States Patent [19]

Smith

[11] Patent Number: 4,513,747
[45] Date of Patent: Apr. 30, 1985

[54] HARD TISSUE SURGICAL NEEDLE

[75] Inventor: Daniel J. Smith, Englishtown, N.J.

[73] Assignee: Ethicon, Inc., Somerville, N.J.

[21] Appl. No.: 436,221

[22] Filed: Oct. 22, 1982

[51] Int. Cl.³ .............................................. A61B 17/06
[52] U.S. Cl. ..................................................... 128/339
[58] Field of Search ............... 128/339, 303.18, 329 A

[56] References Cited

U.S. PATENT DOCUMENTS

| | | | |
|---|---|---|---|
| 1,599,059 | 9/1926 | Morton . | |
| 2,838,049 | 6/1958 | Eisenhofer et al. | 128/305 |
| 2,869,550 | 1/1959 | Kurtz | 128/339 |
| 3,038,475 | 6/1960 | Orcutt | 128/339 |
| 3,094,123 | 6/1963 | Kurtz | 128/339 |
| 3,636,955 | 1/1972 | Kurtz | 128/305 |
| 4,128,351 | 12/1978 | Kurtz et al. | 128/305 |

FOREIGN PATENT DOCUMENTS 119732 7/1982 Japan .

OTHER PUBLICATIONS

Ethicon Inc., "Lancet Point Profile", Drawing No. A-2459, by J. Klug, 04/13/72.
"Mani", Catalog of Matsutani Company of Japan, 1977.

Primary Examiner—C. Fred Rosenbaum
Assistant Examiner—C. W. Shedd
Attorney, Agent, or Firm—Leonard Kean

[57] ABSTRACT

An improved surgical needle of the type having one or more cutting edges converging towards the needle tip and formed by the intersection of a plurality of planar surfaces, for use in cutting through hard body tissue material. The forward end of the needle has one or more smaller additional cutting edges located at the tip to aid initial insertion into the tissue. These additional cutting edges are formed by at least two additional intersecting planar surfaces at the tip portion. The needle is preferably curved in the reference plane defined by one of the cutting edges and the axis of the needle.

23 Claims, 7 Drawing Figures

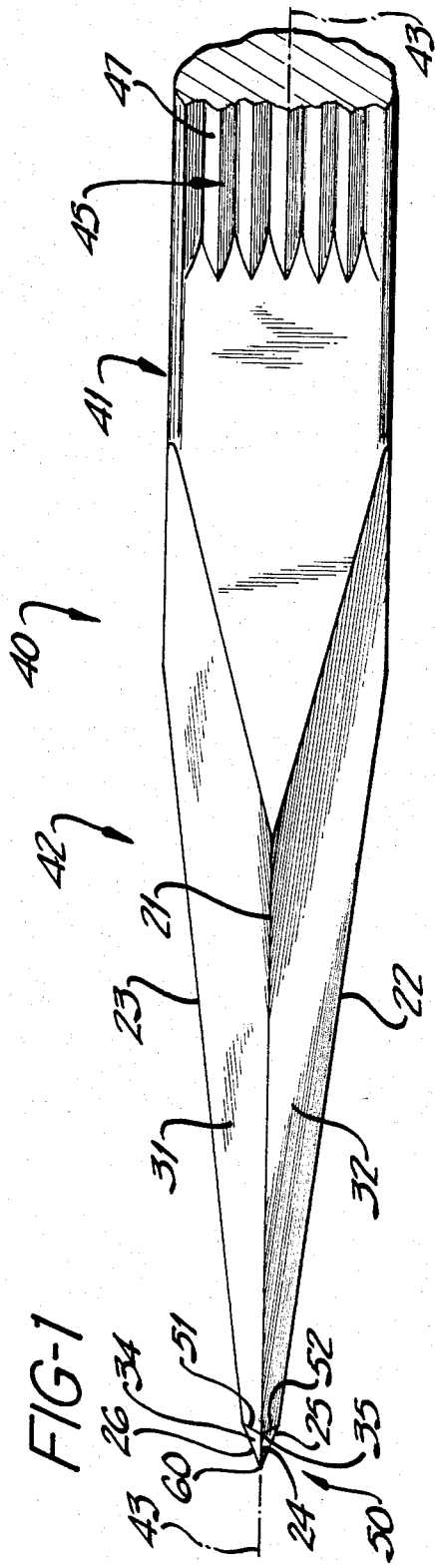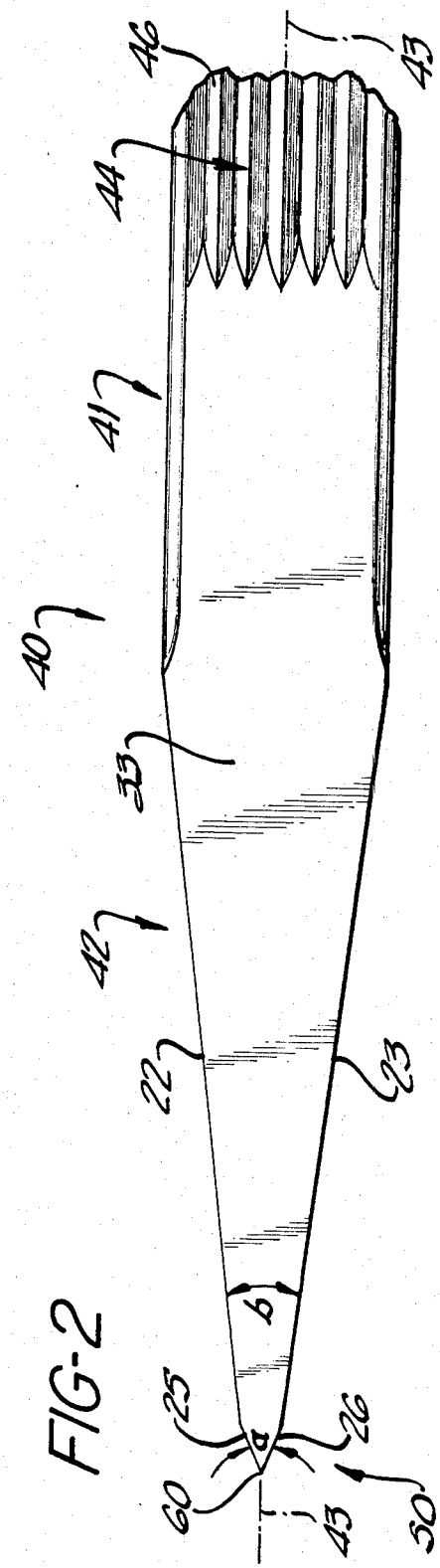

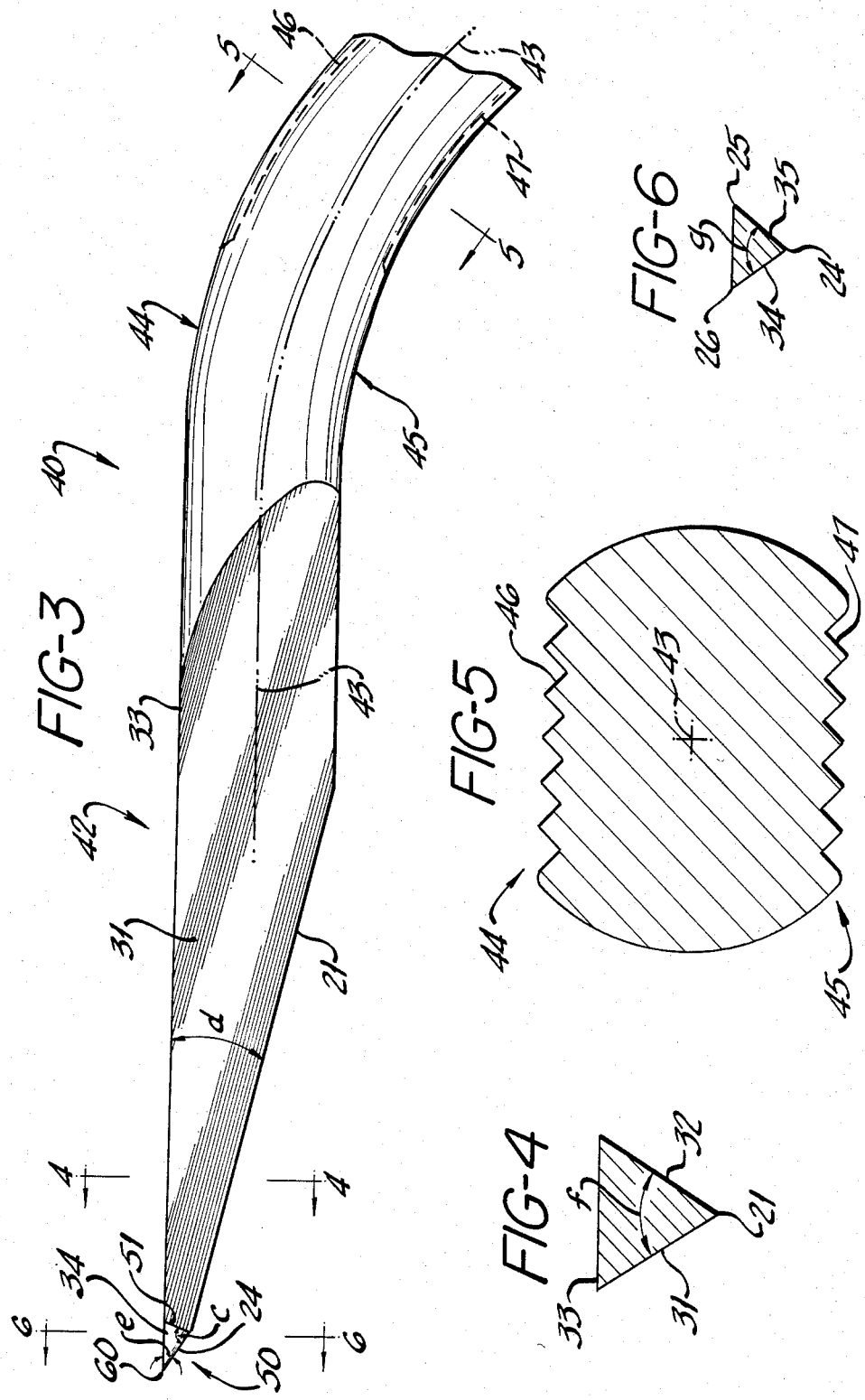

HARD TISSUE SURGICAL NEEDLE

FIELD OF THE INVENTION

This invention relates to surgical needles and in particular to an improved surgical needle for suturing through calcified tissue, cartilage or bone.

DESCRIPTION OF THE PRIOR ART

Surgical needles are required to be as sharp as possible at the tip in order to perform their function properly. Such needles must also be resistant to burr formation caused by an insufficient amount of metal at the extreme tip portion of the needle. In the Kurtz U.S. Pat. Nos. 2,869,550 and 3,094,123, a sharp surgical needle was disclosed, which needle has a single main cutting edge formed by the intersection of two planar surfaces such that the main cutting edge extends from one side of the needle to the other side thereof. In this type of needle greater sharpness is obtained by decreasing the slope angle of the main cutting edge relative to the needle axis. However, as discussed in Kurtz U.S. Pat. No. 3,636,955, as the slope angle is decreased, eventually, so little material is left at the point that the point lacks sufficient structural integrity to effectively penetrate the tissue without the tip of the point burring or otherwise deforming.

In the Kurtz U.S. Pat. No. 3,094,123 the concept of blunting the tip of the needle to avoid deformation of the tip, even when using a fairly sharp slope angle, was disclosed. The Kurtz U.S. Pat. No. 3,636,955 discloses the concept of adding a third planar surface at the extreme tip so as to form a chisel-type cutting edge at the intersection of the third planar surface with one of the first two planar surfaces. However, as the structural strength of the tip portion of the needle has been increased by providing more metal at this area by using either a rounded tip or a chisel-type tip, the amount of force to obtain needle penetration has been increased particularly when calcified tissue has to be penetrated. Thus, there is a need for a surgical needle having a very sharp point but which is still strong enough to retain its structural integrity when used to cut through bone or other hard tissue.

The amount of force required for needle penetration of tissue includes that required for the engagement of the tip of the needle and for the widening of the hole. The widening of the hole is effected either by the blunt dilatation of a conventional taper point needle or by a very sharp cutting action. In the case of a taper point needle, after the tip is engaged, a hole is made by pure blunt dilatation with no cutting action whatsoever. Alternatively, using a needle of the type disclosed in Kurtz U.S. Pat. No. 2,869,550, a hole is produced by initially engaging the tip. The cutting edge of this needle then enlarges the hole and finally the remainder of the hole size is made by blunt dilatation with no cutting edge being present. When the hole is fully developed, the rest of the shaft slides through with friction as the major resistance component. Furthermore, with a conventional cutting edge needle, the relatively sharp edges slide through after the tip is engaged, until there is a fully developed hole. The dilatation per unit time is a direct reflection of the work required, and hence the force required for the needle to make the fully developed hole. With a taper point, the included angle (at the apex of the cone) is approximately 12°. When the needle's included angle is more acute, less work per unit time would be required to make a fully developed hole. However, the more acute the angle, the more fragile the tip, with resultant possible bending over and burr formation, which destroys the sharpness of the needle. When the angle is greater than 12°, the dilatation per unit time must be faster and the needle appears to be more blunt because of the necessity for rapid dilatation. The longer the edge which slips through tissue on entering, the sharper the needle and the less required force per unit time to make a completely developed hole. Furthermore, a sharper needle results in a smaller opening and the minimization of trauma. Kurtz U.S. Pat. No. 4,128,351 is directed to a surgical needle of the type having a single main cutting edge formed by the intersection of two planar surfaces for use in cutting through hard body tissue material. The latter patent discloses a forward end of the needle which includes a single, relatively small additional substantially planar surface having an acute angle of convergence with the axis of the needle and intersecting at substantially equal acute angles with the other two planar surfaces, resulting in a sharp needle with a relatively high resistance to burring.

The Orcutt U.S. Pat. No. 3,038,475 discloses the concept of a triple edged surgical needle, but does not address the problem of the burring of the needle point.

One of the objects of the present invention to provide a triple edged needle which is formed with three smaller additional cutting edges located at the tip in order to aid initial insertion into the tissue. It is a further object of the invention to provide a flattened and ribbed section near the cutting portion of the needle to facilitate positive placement and pick-up during needle penetration through hard tissue.

The needle disclosed in Kurtz U.S. Pat. No. 4,128,351, being conventionally ground on only two sides, has a portion of the needle circumference remaining so that it contains only one main cutting edge (apart from the small cutting edges at the forward end of the needle), whereas the preferred embodiment of the present invention provides three main cutting edges (apart from three smaller additional cutting edges at the forward end of the needle). The tip of one of the embodiments of the needle of Kurtz U.S. Pat. No. 4,128,351 terminates at the intersection of the needle's centroidal axis and its main cutting edge; whereas in the case of the present invention, the tip of the needle terminates at the intersection of the main cutting edge and the outer periphery of the needle.

Although the preferred needle of the present invention is triple edged with three smaller additional cutting edges located at the tip, nevertheless the invention includes needles formed with fewer than three edges, and in which there are at least two additional intersecting planar surfaces at the tip portion, forming one or more additional cutting edges.

According to the present invention there is provided a surgical needle comprising a body portion, an adjacent cutting portion which terminates near the tip of the needle and a tip portion, there being a plurality of planar surfaces forming one or more cutting edges in the cutting portion, which cutting edges converge towards the tip of the needle, there being at least two additional intersecting planar surfaces at the tip portion of the needle forming one or more additional cutting edges.

According to a preferred embodiment of the present invention, there is provided a surgical needle comprising a body portion and an adjacent cutting portion which terminates at the tip of the needle, the cutting portion having top and bottom surfaces, there being first, second and third intersecting planar surfaces forming three cutting edges in the cutting portion, which cutting edges converge towards the tip of the needle, the first and second planar surfaces being formed on the bottom of the cutting portion and defining the first cutting edge, and the third planar surface being formed on the top of the cutting portion and defining second and third cutting edges. According to the most preferred embodiment of the present invention, there are fourth and fifth intersecting planar surfaces at the tip of the needle forming three additional cutting edges, the fourth and fifth planar surfaces being formed on the bottom of the cutting portion and defining a fourth cutting edge which extends from the forward end of the first cutting edge to the tip of the needle, the fourth and fifth planar surfaces forming together with the third planar surface, fifth and sixth cutting edges respectively, which converge to the tip of the needle, the angle between the fifth and sixth cutting edges being greater than the angle between the second and third cutting edges. The angle of slope of the first cutting edge is preferably less than 20°.

The side of the needle having the above metioned first or main cutting edge is referred to herein as the "bottom" of the needle and the plane defined by said main cutting edge and the axis of the needle point or tip is referred to as the "reference plane" so that when the main cutting edge is on the bottom, the reference plane is vertical. By convention, the angle between the main cutting edge and the upper, outer periphery of the needle is termed the "angle of slope". This angle determines the rate at which the tissues are cut, to the diameter of the needle. The angle of slope must be minimized in order to provide for ease of passage of the needle through the tissue and yet must be sufficiently large to preserve metal at the point of the tip to give the needle rigidity. In the present invention, it is preferable that the angle of slope be less than 20°.

The needle of the present invention is preferably curved in the reference plane defined by the first cutting edge and the longitudinal axis of the needle. The fourth cutting edge which extends from the first cutting edge should also lie in the reference plane. It is furthermore preferred that the third planar surface be positioned such that a fictive straight line "L" (which is formed by the intersection of the reference plane and the third planar surface), is substantially parallel to the central axis of the needle.

The angle of slope of the first cutting edge desirably varies between 8° and 20° (and more preferably between 11° and 13°).

The angle between the second and third cutting edges should desirably be between 10° and 25° (and more preferably between 12° and 15°).

The angle between the fifth and sixth cutting edges is desirably between 30° and 60° (and more preferably 30° and 45°). Furthermore, the angle between the fourth cutting edge and the line formed by the intersection of the first and fourth planar surfaces is desirably between 30° and 130° (and more preferably between 60° and 110°).

The angle between the first and second planar surfaces is termed the "sharpness angle and should desirably be between 50° and 70° and is preferably between 55° and 65°. The preferred surgical needle of the present invention has three long cutting edges formed by the intersection of three planar surfaces, as well as three secondary edges presenting different angles located near to the tip of the needle. This needle permits a long cutting action and yet with much less likelihood of bending or deformation of the tip. The foregoing and other objects and advantages of the present invention are discussed in or will become apparent from the detailed description of the preferred embodiment hereinbelow.

BRIEF DESCRIPTION OF THE DRAWINGS

In the drawings, in which like numerals represent like elements in the several views:

FIG. 1 is a bottom view of the cutting portion of a surgical needle of the present invention.

FIG. 2 is a top view of the needle of FIG. 1.

FIG. 3 is a side view of the needle of FIG. 1.

FIG. 4 is a cross-sectional view taken along line 4—4 of FIG. 3.

FIG. 5 is a cross-sectional view taken along line 5—5 of FIG. 3.

FIG. 6 is a cross-sectional view taken along line 6—6 of FIG. 3.

DETAILED DESCRIPTION OF THE PREFERRED EMBODIMENT

Figure 7:
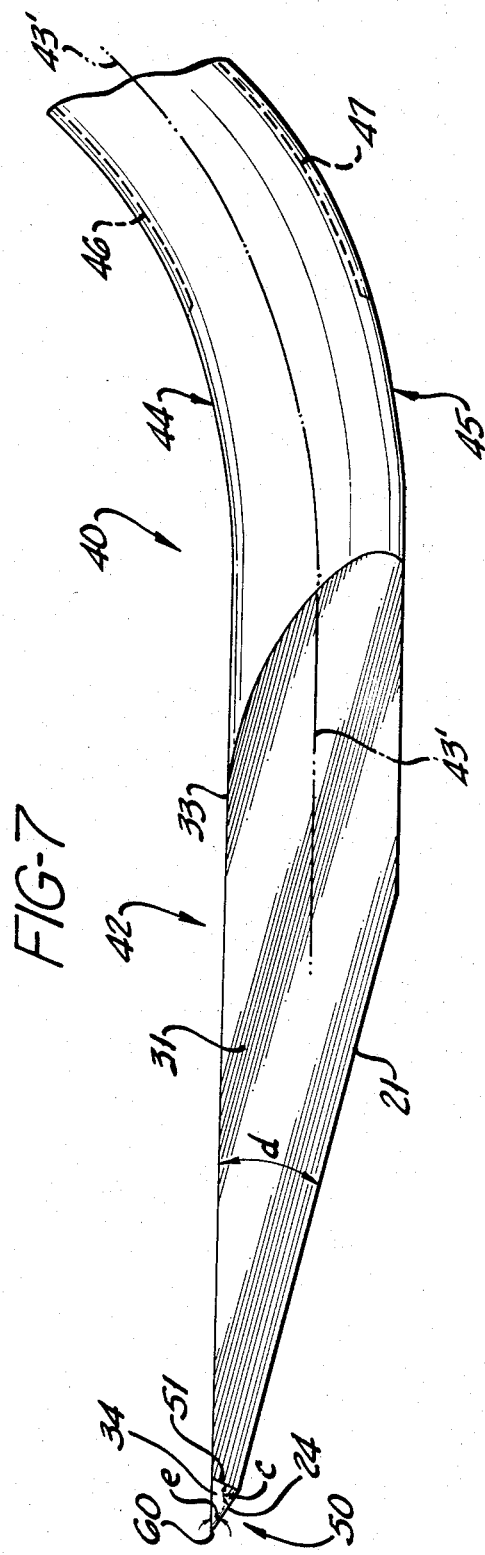
FIG. 7 is a side view of a modified embodiment of the needle of FIG. 1.

A surgical needle 40, according to the present invention, is illustrated in FIGS. 1 through 6. Needle 40 includes a body portion 41 and a cutting portion 42 and has a curved axis 43 (see FIG. 3) which defines a reference plane. As will be seen from FIG. 7 (which shows a modified embodiment of the needle of FIG. 1), the needle 40 may optionally be curved in a direction opposite to that of the needle shown in FIG. 3 and will have a curved axis 43' which nevertheless lies in the same reference plane as that defined by axis 43 (as shown in FIG. 3). A main cutting edge 21 is formed in a conventional manner at the bottom of said cutting portion 42 by the intersection of a first substantially planar surface 31 and a second substantially planar surface 32 (FIG. 1). Thus it can be seen that main cutting edge 21 lies in the reference plane as shown in FIG. 3. Secondary cutting edges 22 and 23 are formed by the intersection of a third substantially planar surface 33 (on the top of the cutting portion 42), with planar surfaces 31 and 32 respectively (FIG. 2).

Cutting portion 42 includes an end portion 50 and a tip 60, the longitudinal axis of the needle being designated 43. Substantially planar surfaces 34 and 35 are formed at the bottom of end portion 50, thus creating three additional cutting edges 24, 25 and 26 (FIGS. 1, 2 and 3). It will be noted that cutting edge 24 constitutes an extension of cutting edge 21 (FIG. 3) and said cutting edge 24 extends to the tip 60 which lies at the intersection of the reference plane and planar surface 33 (FIG. 2). It will also be noted that the angle "a" between cutting edges 25 and 26, is necessarily greater than the angle "b" between cutting edges 22 and 23 (FIG. 2). Said angle "a" is between about 30° and 60° and is preferably between 30° and 45°; whereas said angle "b" is between about 10° and 25° and is preferably between 12° and 15°.

It will be noted from FIGS. 1 and 3 that the intersection between planar surface 31 and planar surface 34 forms an edge 51; and the intersection between planar surface 32 and planar surface 25 forms an edge 52. The angle "c" between edge 51 and cutting edge 24 is preferably between about 60° and 110° and can range from about 30° and 130°.

The angle of slope "d" between cutting edge 21 and planar surface 33 (as measured along the reference plane) is less than 20° and is preferably between 11° and 13°. the angle "e" between cutting edge 24 and planar surface 33 as measured along the reference plane is less than 45° and is preferably between 30° and 37°.

It will be noted that the tip of the needle 60 lies in the planar surface 33 and is thus displaced from the central axis 43 of the needle. In this connection, the planar surface 33 is positioned such that the fictive straight line "L" (which is formed by the intersection of the reference plane and planar surface 33) is substantially parallel to the central axis 43 (FIG. 3).

All of the planar surfaces 31, 32, 33, 34 and 35 are preferably formed, and then ground.

FIGS. 5 and 4 depict the cross-sectional shapes of needle 40 at two locations along the body portion 41 and the cutting portion 42 (FIG. 3). Needle 40 is generally round in cross-section with a flattened section at 44 and also at 45, to increase needle holder stability. In this connection, elongated grooves 46 and 47 may also be formed in the flattened portions 44 and 45, for additional stability. Said grooves 46 and 47 are indicated in FIG. 2 and FIG. 1 respectively.

FIG. 5 depicts the cross-sectional shape of the needle, illustrating the flattened portions 44 and 45 (see FIG. 3). Grooves 46 and 47 are also illustrated in FIG. 5.

FIG. 4 depicts the cross-sectional shape of the needle 40 at the cutting portion 42. It will be noted that said cross-sectional shape is substantially that of an equilateral triangle, so that the sharpness angle between the first and second planar surfaces 31 and 32, is between 55° and 65°. However, this sharpness angle may be varied between 50° and 70°. The sharpness angle is designated as "f" in FIG. 4.

FIG. 6 depicts the cross-sectional shape of needle 40 at the forward tip thereof. The sharpness angle "g" desirably varies between 50° and 70° and most preferably is between about 55° and 65°.

With respect to the sharpness angle "f" (FIG. 4) if it should be made too small, there would be insufficient metal in the forward end of the needle to give the point the necessary strength. Similarly the angle of slope "d" (FIG. 3) should be minimized in order to provide for ease of passage of the needle through the tissue and yet must be sufficiently large to perserve metal at the tip to give the needle sufficient rigidity. The needle of the present invention 40 performs best when the sharpness angle is within the range of 50° to 70° and is preferably between about 55° and 65°.

The provision of the forward tip 50 (FIGS. 1, 2 or 3), not only provides additional independent cutting edges but enables the needle 40 to resist burring when it is used in hard tissue. At the same time, however, the needle 40 has a low insertion and penetration force requirement and thus creates a minimal amount of trauma.

STERNOTOMY PERFORMANCE COMPARISON;

Penetration through Polyurethane

In order to determine the relative ease of penetration of a polyurethane pad, demonstrated by the present needle as compared to that demonstrated by a needle such as that disclosed in the Kurtz U.S. Pat. No. 4,128,351, the following tests were conducted:

A polyurethane pad was mounted over an Instron load cell. Needles which were handheld, were penetrated through the polyurethane pad and the average peak forces were measured. The needle of the present invention (60 mil), made of stainless steel was compared with a Deknatel sternotomy, stainless steel needle, (60 mil), designated K-60. Both types of needles were initially stripped clean and siliconed so as to ensure that the lubrication was comparable in each case.

Five different needles of each type were tested and three tests were conducted with respect to each. After averaging the results of all of the tests, the average force required for the present needle to penetrate the polyurethane pad was 7.9 pounds; whereas the average force required for the Deknatel K-60 needle to penetrate the same polyurethane pad was determined to be 11.45 pounds. Said Deknatel K-60 needle is similar in shape to that shown in FIG. 5 of the aforementioned Kurtz U.S. Pat. No. 4,128,351. It will be noted that it is not feasible to use an actual sternum for conducting these tests, due to the lack of uniformity along its length.

I claim:

1. A surgical needle, comprising a body portion, a contiguous cutting portion which terminates near the tip of the needle and a tip portion, there being a plurality of planar surfaces forming cutting edges in said cutting portion, which cutting edges converge towards the tip of the needle, there being at least two additional planar surfaces intersecting in the tip portion of the needle forming additional cutting edges at the intersection between said additional planar surfaces and at intersections between said additional planar surfaces with selected ones of said plurality of planar surfaces.

2. The needle of claim 1, in which the cutting portion has top and bottom surfaces, there being first, second and third intersecting planar surfaces forming three cutting edges in said cutting portion, the first and second planar surfaces being formed on the bottom of said cutting portion and defining a first cutting edge, and the third planar surface being formed on the top of said cutting portion and defining second and third cutting edges.

3. A surgical needle, comprising a body portion having upper and lower surfaces and a contiguous cutting portion which terminates at a tip portion of the needle, said cutting portion having top and bottom surfaces which are contiguous, respectively to said upper and lower surfaces of said body portion, there being first, second and third intersecting planar surfaces forming three cutting edges in said cutting portion, which cutting edges converge towards the tip of the needle, said bottom surface comprising said first and second planar surfaces defining a first cutting edge which has a forward end contiguous to said tip portion and a rear end, and the third intersecting planar surface defining said top surface which has second and third cutting edges; said tip portion having fourth and fifth intersecting planar surfaces forming three additional cutting edges, the intersection of the fourth and fifth planar surfaces defining a fourth cutting edge which extends from the forward end of said first cutting edge to the tip of the needle, the intersections of said fourth and fifth planar surfaces with said top surface defines respectively fifth and sixth cutting edges which converge to the tip of the needle, the apex angle between the fifth and sixth cutting edges being greater than the apex angle between the second and third cutting edges.

4. The needle of claim 3, at least a portion of said body portion of said needle having a curved longitudinally extending axis defining a "reference plane", said first cutting edge being colinear to a line in said "reference plane", said "reference plane" being substantially perpendicular to said top surface, said upper and lower surfaces of said body portion being curved.

5. The needle of claim 4, wherein both the first and the fourth cutting edges lie in said "reference plane".

6. The needle of claim 5, wherein the third planar surface is positioned such that a straight line "L" (which is formed by the intersection of the reference plane and said third planar surface) is colinear with the immediately contiguous curved line "M" formed by the intersection of the "reference plane" and the upper curved surface of said body portion, said straight line "L" constituting a tangent to curved line "M", so that if said body portion were to be straightened, said line "L" would be parallel to said axis.

7. The needle of claim 5, wherein the angle of slope of the forth cutting edge is less than 45°, said "angle of slope" being defined as the angle between said cutting edge and said top surface, in said "reference plane".

8. The needle of claim 7, wherein the angle of slope of the fourth cutting edge is between 30° and 37°.

9. The needle of claim 4, wherein the angle of slope of the first cutting edge is between 8° and 20°, said "angle of slope" being defined as the angle between said cutting edge and said top surface, in said "reference plane".

10. The needle of claim 9, wherein the angle of slope of the first cutting edge is between 11° and 13°.

11. The needle of claim 4, said axis being curved in a circle having a given radius and a given center, said lower surface being located on the inside of the needle radius so that said lower surface is closer to said center of said circle than is said upper surface, portions of both the upper and lower surfaces of said body portion being flattened to increase needle holder stability.

12. The needle of claim 4, said axis being curved in a circle having a given radius and a given center, said lower surface being located on the outside of the needle radius so that said upper surfave is closer to said center of said circle than is said lower surface, portions of both the upper and lower surfaces of said body portion being flattened to increase needle holder stability.

13. The needle of claim 11 or 12 in which grooves are formed in said flattened surfaces of said body portion for additional needle holder stability.

14. The needle of claim 3, wherein the apex angle between the second and third cutting edges is between 10° and 25°.

15. The needle of claim 14, wherein the apex angle between the second and third cutting edges is between 12° and 15°.

16. The needle of claim 3, wherein the apex angle between the fifth and sixth cutting edges is between 30° and 60°.

17. The needle of claim 16, wherein the apex angle between the fifth and sixth cutting edges is between 30° and 45°.

18. The needle of claim 3, wherein the angle between the fourth cutting edge and the line formed by the intersection of the first and fourth planar surfaces is between 30° and 130° included.

19. The needle of claim 18, wherein the angle between the fourth cutting edge and the line formed by the intersection of the first and fourth planar surfaces is between 60° and 110°.

20. The needle of claim 3, wherein the "dihedral angle" between the first and second planar surfaces is between about 50° and 70°.

21. The needle of claim 20, wherein the "dihedral angle" between the first and second planar surfaces is between about 55° and 65°.

22. The needle of claim 3, wherein the "dihedral angle" between the fourth and fifth planar surfaces is between about 50° and 70°.

23. The needle of claim 22, wherein the "dihedral angle" between the fourth and fifth planar surfaces is between about 55° to 65°.

* * * * *

UNITED STATES PATENT AND TRADEMARK OFFICE
CERTIFICATE OF CORRECTION

PATENT NO. : 4,513,747
DATED      : April 30, 1985
INVENTOR(S) : Daniel J. Smith It is certified that error appears in the above-identified patent and that said Letters Patent is hereby corrected as shown below:

On the title page, Item [56] insert:

-- 3,834,599   9/1974   Herr........223/102 --.

Item [22] should read

-- Field:   Oct. 25, 1982 --.

Column 8, Claim 12, line 2, "surfave" should read -- surface --.

Signed and Sealed this

Eighth Day of July 1986

[SEAL]

Attest:

DONALD J. QUIGG

Attesting Officer

Commissioner of Patents and Trademarks